United States Patent [19]
Kutsuma

[11] Patent Number: 5,905,652
[45] Date of Patent: May 18, 1999

[54] SYSTEM FOR PREPARING MATERIALS FOR GUIDING A PATIENT IN TAKING MEDICINE

[75] Inventor: Nobuaki Kutsuma, Saitama-ken, Japan

[73] Assignee: Kabushiki Kaisha Asahi, Ohmiya, Japan

[21] Appl. No.: 08/890,462

[22] Filed: Jul. 9, 1997

[30] Foreign Application Priority Data

Sep. 13, 1996 [JP] Japan .................................. P8-243006

[51] Int. Cl.⁶ .................................................. G06F 17/00
[52] U.S. Cl. ............................... 364/479.05; 364/479.01; 221/5
[58] Field of Search .............................. 364/400, 479.01, 364/479.05; 206/534; 221/5, 2; 235/375; 283/67, 900; 383/105, 106

[56] References Cited

U.S. PATENT DOCUMENTS

| | | | |
|---|---|---|---|
| 4,918,604 | 4/1990 | Baum | ........................................... 221/5 |
| 5,390,796 | 2/1995 | Kerfoot, Jr. | ............................... 206/534 |
| 5,597,995 | 1/1997 | Williams et al. | ........................ 235/375 |

*Primary Examiner*—William Grant
*Assistant Examiner*—Steven R. Garland
*Attorney, Agent, or Firm*—Nikaido, Marmelstein, Murray & Oram LLP

[57] ABSTRACT

A system for guiding the taking of medicine having a host computer, a personal computer connected to the host computer, and a color printer connected to the personal computer producing a document or a medicine bag with guiding instructions for taking medicine prepared by the system printed thereon. The host computer is used for inputting prescription information for a patient by a doctor. The input information are transmitted to the personal computer from the host computer. The pharmacist edits the information received from the host computer to prepare the medicine bag and/or document by printing the edited guiding instructions for taking medicine inclusive of visual image of each drug thereon.

5 Claims, 6 Drawing Sheets

FIG. 4

To : (     Name     )

(    Direction for use and dose    )

| Name and inf. | Drug | Morn. | Noon | Even. |
|---|---|---|---|---|
| (Drug A)<br>(Efficacy)<br>10mg | ○ | 1 | | 1 |
| (Drug B)<br>(Efficacy)<br>Capsule | ⬬ | 2 | | 2 |
| (Drug C)<br>(Efficacy)<br>20mg | —<br>○ | Dose 1 tablet three times in a day for every 8 hours. |||

(Pharmacy's name)
(Domicile)
(Dates)

(    Signature    )

FIG. 5

To : ( _____Name_____ )

| Medicine | Direction for use |
|---|---|
| ○○○○ 1% solution | Drop lotion in your eyes for 4 or 5 times in a day. |
| △△△△ ointment 5mg | Apply ointment to your eyes for several times in a day. |

(Pharmacy's name)
(Domicile)
(Dates)

( _____Signature_____ )

40

SYSTEM FOR PREPARING MATERIALS FOR GUIDING A PATIENT IN TAKING MEDICINE

BACKGROUND OF THE INVENTION

The present invention relates to a system for guiding a patient in taking medicine by preparing a document based on prescription information from a doctor and other information about the medicine, and a medicine bag with such information printed thereon.

Generally, medicine for a particular patient is dispensed by a pharmacist based on a prescription prepared by a doctor, and handed to the patient in a medicine bag on which is information concerning dose and the directions for use. Two or more different drugs can be contained in the prescribed medicine and a medicine bag is prepared per each drug.

For instance, when a doctor prescribes to a patient that one each tablet X and tablet Y is to be taken after each meal, and one tablet Z is to be taken every 8 hours, these medicines are held in different medicine bags to avoid mistakes in taking the medicine, namely one bag for the tablets X and Y and the other bag for the tablet Z. The information on the bag accommodating the tablets X and Y is described as "Dose one tablet after each meal", and on the other bag accommodating the tablet Z, as "Dose one tablet every 8 hours", respectively.

However, when there are various drugs which are different in dose and directions for use thereof, a medicine bag must be prepared for each drug. The dose and directions for use must be described on each bag, thereby causing an increase in number of medicine bags produced.

Although it may be possible to accommodate all of the drugs in one medicine bag, it is usually hard for patients to correctly identify actual drugs from the name indicated on the medicine bag. Accordingly, this could cause mistakes in dose and/or use on taking the medicine even if the medicine bag has the information as to the relations between each drug's name and information of dose and use. For instance, when tablets X and Y are to be dosed every meals and tablet Z is to be dosed with a time interval of 8 hours and are accommodated in the same bag, a mistake that the tablet X or Y is taken every 8 hours or the tablet Z is taken at each meal can occur. This is especially liable to occur when there are various plural drugs different in dose and use. It would be more likely to cause confusion and resultingly cause mistakes in their dose and/or use.

When there are plural medicine bags, or when a patient is under the care of two or more doctors and given medicines through two or more pharmacists, it is likely that the patient carelessly takes out plural drugs from each medicine bag at the same time and may erroneously put a certain drug back into a different medicine bag. In such a case, it is difficult to dose the drugs according to prescription therefor and a dangerous result may occur.

SUMMARY OF THE INVENTION

An object of the invention is to provide a guiding system for taking medicine to prepare a document having printed concrete information on prescribed drugs for solving the problems referred to above.

Another object of the invention is to provide a medicine bag having such information printed thereon.

According to the invention, the first object can be attained by a guiding system for dispensing and taking medicine which comprises certain particular structure. A computerized management section has means for a doctor to directly input information about a patient and a prescription for the patient, means for displaying the prescription information, and a main memory to store information of the prescription for each patient. A computerized editing section is connected to the management section and has memory means to store information about numerous drugs inclusive of a visual image of each drug, means for accessing the main memory in the management section and the memory means storing information on the drugs and for integrating and editing the information of the prescription of the patient and the information about the particular drugs, and means for displaying information obtained from the means for accessing, integrating and editing. A printing means is connected to the editing section to print out information edited in the editing section and including matters to identify each prescribed drug, dose and directions for use thereof as well as the visual image of each of the drug(s) external appearances correlated together with patient information.

With this arrangement, the input prescription information is edited correlating each drug name therein with the corresponding image of the external appearance in the memory of the editing section to print out the edited guiding instructions in a form for taking medicine including the visual image of the respective drug's external appearance, thereby allowing the preparation of an instruction document and/or medicine bag having such information. The resulting document or medicine bag makes the relationships between a drug's name and information of dose and use so clear because of the image of each drug's external appearance shown on the instruction document and/or medicine bag, that accordingly it becomes easy for patients to identify a correct drug in a medicine bag among plural ones. This prevents confusion and mistakes in dose and use on taking medicine.

The editing section may have a means for inputting a visual image of drug, which can be selected from the group consisting of a digital camera, a video camera, a CCD camera and an image scanner. Such image inputting means enable adding drug's external appearances as visual image data in the memory of the personal computer.

Also, the information on the visual image of each drug may be that of a packaged state. Such packaged state image is helpful for patient to recognize the drug correctly when the drug is a packaged one.

Further, the above information on drug may include information concerning the efficacy of a main effective ingredient contained therein. Such information is useful for informed consent of the patient.

The second object of the invention can be attained by printing the edited information onto a paper bag using the above system, thereby preparing a medicine bag having printed thereon the efficacy of the drug, full-colored packaged state of the drug and so forth. Such medicine bag enables the patient to identify each of the actual drugs in the bag by checking the same while referring to the visual image thereof printed on the bag prior to taking the drug and allow the patient to take the same in accordance with directions for use correctly preventing confusion and mistakes.

BRIEF DESCRIPTION OF THE DRAWINGS

FIG. 4 is a front view of a medicine bag, on which various information are printed out by using the guiding system for taking medicine of the invention.

FIG. 5 is a front view of another medicine bag similar to that in FIG. 4.

DETAILED DESCRIPTION OF PREFERRED EMBODIMENTS

Figure 1:
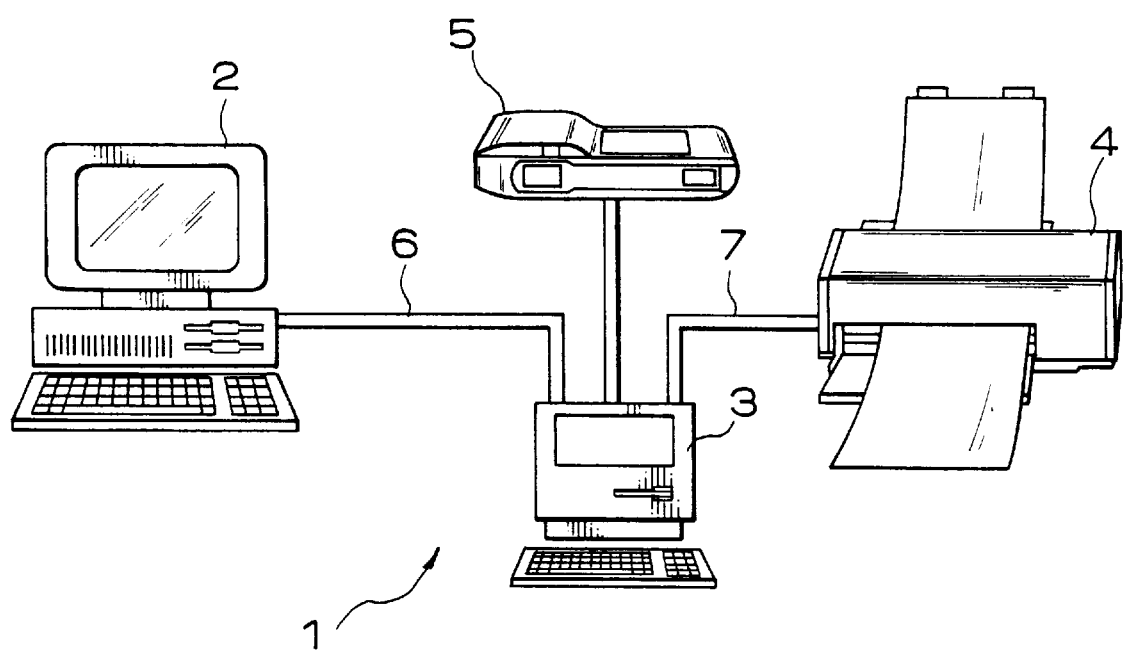
FIG. 1 is a diagrammatic illustration showing an arrangement of machines or tools to compose a guiding system for taking medicine of the invention.

As seen from FIG. 1, a guiding system for taking medicine 1 according to the invention basically comprises a host computer 2, a personal computer 3 and a color printer 4 connected in series to each other. A digital camera 5 may be connected to the personal computer 3.

The host computer 2 is operated by a doctor or an operator for the doctor to directly input information for preparing a prescription for each patient based on the diagnosis and to store the same. The doctor may access to the stored data such as the administration history of his patient to utilize the same for preparing an updated prescription for the patient. The host computer 2 has also a function for transmitting information on prescription and medicine administration to the personal computer 3 through a serial line 6 or a local area network (LAN).

The personal computer 3 is installed in a pharmacist office of the hospital or another specified drugstore to receive information on the prescription and medicine administration transmitted from the host computer 2 to store the same in memory means incorporated therein. The personal computer 3 has the functions to input and store image data of each drug's external appearance and information related thereto and to show the same on a displaying means. An operator of the personal computer 3 can edit the data and information in an appropriate form to output the edited information to the color printer 4.

Although the host computer 2 and personal computer 3 are usually connected by the serial line 6 or LAN, these may be connected through a public telephone line using appropriate technology.

The color printer 4 is connected to the personal computer 3 through a parallel cable 7 to receive the edited information from the personal computer 3 for printing the same in full-color on a prescribed paper sheet or a medicine bag.

The digital camera 5 is connected to the personal computer 3 through a cable and a program control (PC) card inserted in a card slot of the computer, so that a visual image data shot by the camera can be transmitted to the personal computer 3. Instead of the digital camera 5, a 8mm video camera or a CCD video camera may be used. In such case, a video capture board is incorporated in the personal computer 3 to convert a moving image before transmission to a stationary image. Further, an image scanner may also be used.

Figure 2:
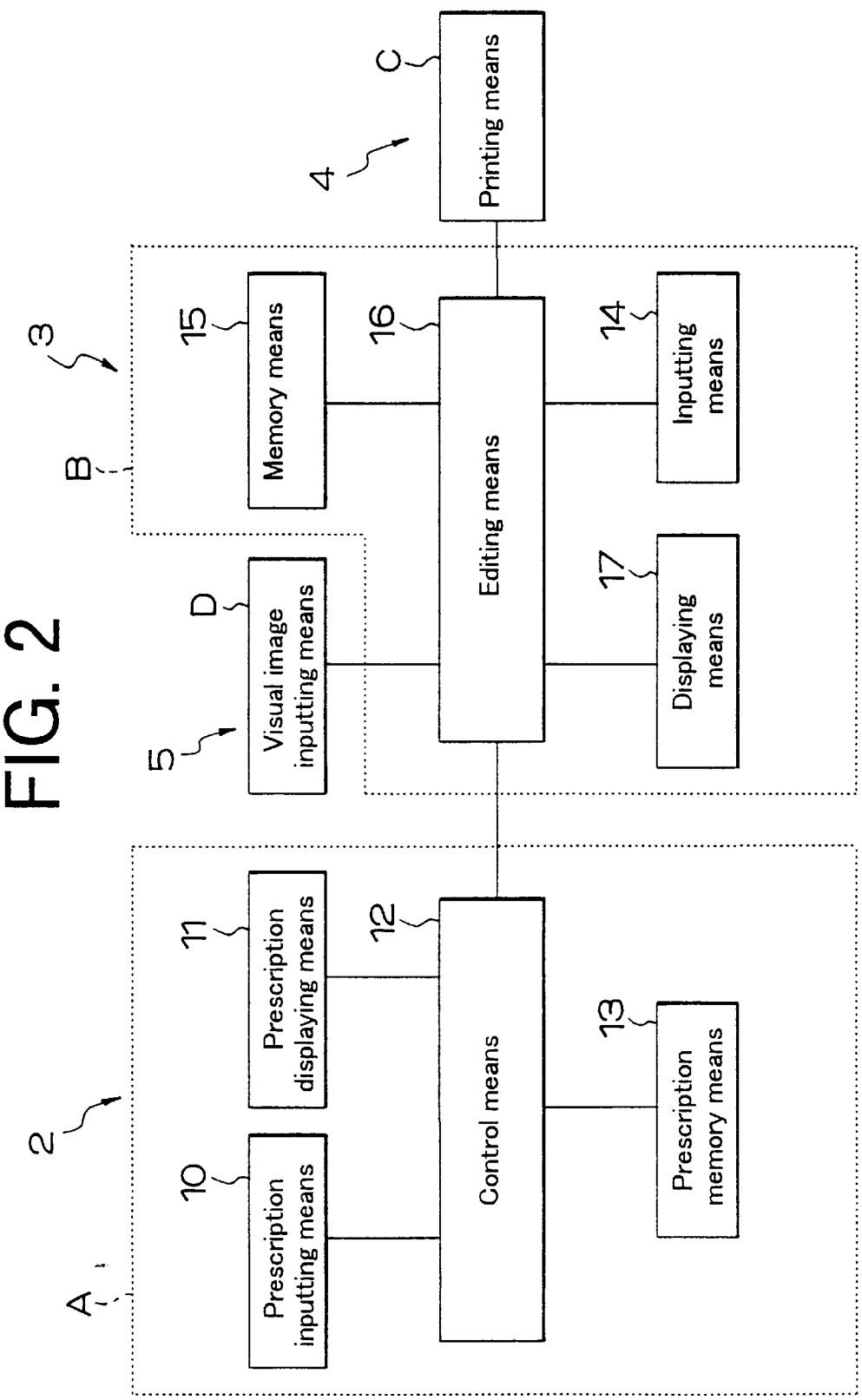
FIG. 2 is a functional block diagram of the guiding system for taking medicine according to the invention.

Referring to FIG. 2, the following describes the functions of the system having the structural arrangement set forth above. This arrangement comprises a management section A for managing prescription information for each patient, an editing section B for receiving an updated prescription information from the management section A and editing a medicine administration guiding instructions according to the information from the management section A and information on drugs stored in memory means incorporated therein, printing means C for printing out the information in a form edited in the editing section B, and a visual image inputting means D for shooting and inputting a visual image of drug's external appearance to be additionally stored.

The management section A comprises an inputting means 10 for inputting information on a prescription for a patient, an displaying means 11 for indicating or showing input information, a control means 12 for controlling input or output of the information, and a memory means 13 for storing the input information on the prescription.

The inputting means 10 is used for inputting information on the prescription to the host computer 2, which prescription has been prepared by a doctor based on the diagnosis of a patient. As the inputting means, a keyboard belonging to the host computer 2 is used as shown in FIG. 1, but a mouse, light pen, digitizer/ tablet or the like can be used.

The displaying means 11 is used for indicating information on the prescription by the doctor and may be of a cathode ray tube (CRT) display or the like connected to the host computer 2.

The control means 12 has the functions of temporary storing information input by the inputting means 10, and transmitting the information to the displaying means 11 to indicate the same, and comprises a CPU, memory and the like incorporated in the host computer 2.

The memory means 13 is used for storing information of the input prescription on each patient and may be of a magnetic disc or the like connected to the host computer 2.

The editing section B comprises an inputting means 14, memory means 15, editing means 16 and displaying means 17. The editing section B can display the received prescription information of a specific patient on the displaying means 17, name and efficacy of various drugs and a visual image thereof recorded in the memory means 15 preliminarily to indicate such information on the displaying means 17 for editing the desired guiding instructions for taking the medicine which includes a content of the prescription. Visual image inputting means D such as the digital camera 3 shown in FIG. 1 belongs to the editing section B to obtain an image data of a drug's external appearance newly put on sale. The data is transmitted to and stored by the memory means 15. Information of the new drug other than image data are input by the inputting means 14 and stored in the memory means 15. After the editing, the information indicated in a form on the displaying means 17 is transmitted to the printing means C and is printed out by operation of the inputting means 14.

As shown in FIG. 1, a keyboard may be used as the inputting means 14 attached to the personal computer 3. The memory means 15 may be of a hard disc incorporated in the personal computer 3. The editing means 16 comprises a CPU, memory and the like incorporated in the personal computer 3 as well as a PC card inserted into a card slot of the personal computer 3. The displaying means 17 is a full-colored CRT display of the personal computer 3, which has a high resolution to clearly indicate the visual image of drug. The printing means C is a color printer which has ability to print out information not only on a sheet of paper but also on a paper bag.

Figure 3:
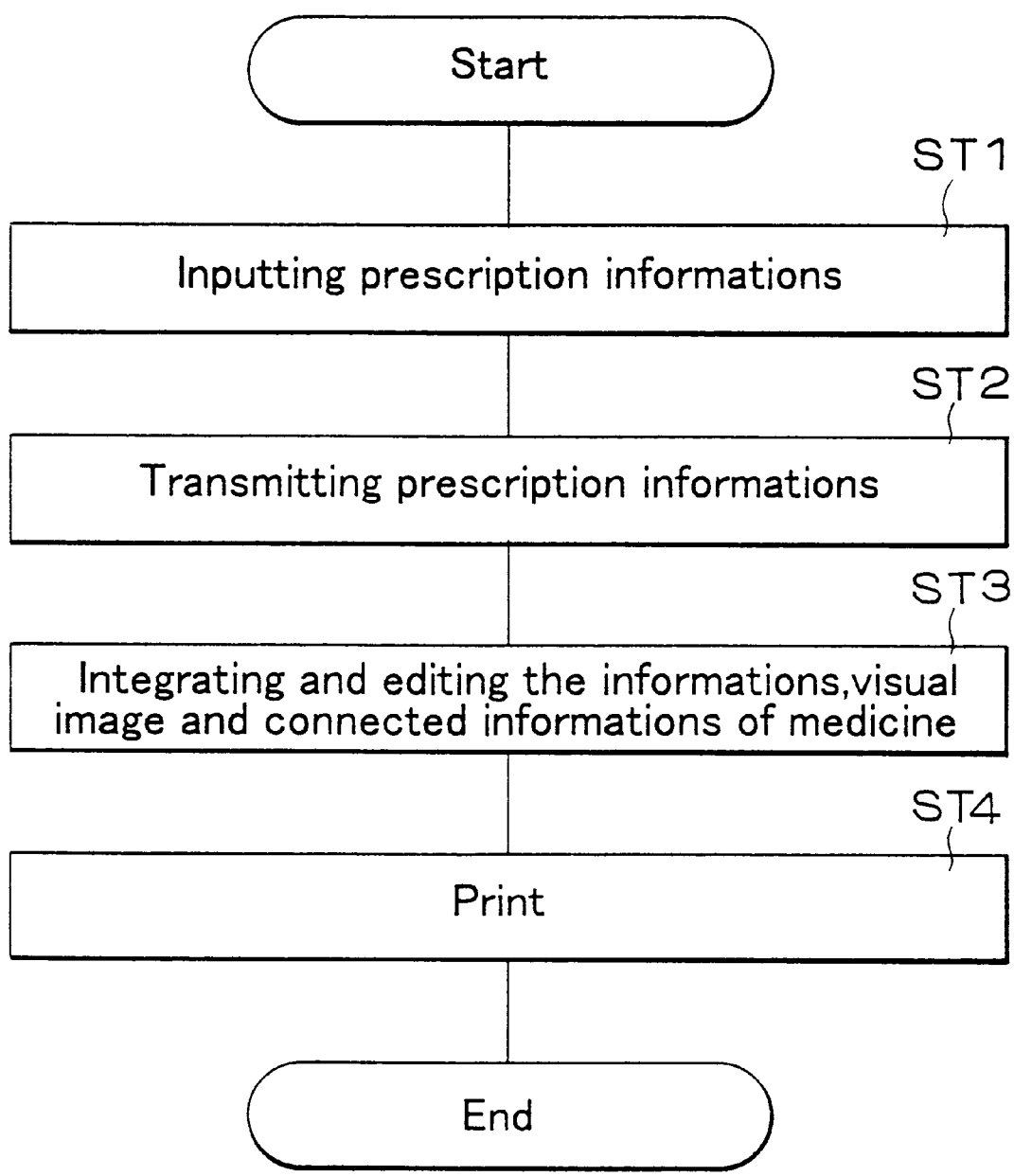
FIG. 3 is a flow chart showing operations of the guiding system for taking medicine of the invention.

Referring to FIG. 3, a flow chart is shown to explain steps from inputting information on a prescription for a patient to printing out guiding instructions for a patient to take medicine on a paper bag at a medical office to prepare a medicine bag.

A host computer 2 is put on a desk of the doctor who examines and diagnoses a patient to prepare a prescription for the patient. In the first step ST 1, the doctor inputs prescription information by operating the inputting means 10, while indicating the input information on the display means 11 under control of the control means 12. The doctor can access to the memory means 15 in the editing section B to check a kind of drugs to be prescribed and also can access to the memory means 13 in the management section A to check the latest prescription or history of prescriptions for the patient, for his reference, to prepare and store an updated prescription.

In the second step ST 2, the data of prescription information prepared and stored in a built-in memory of the host computer 2 is transmitted by the doctor to the memory means 15 of the personal computer 3. The transmission may be effected also by control of the personal computer 3. In that case a pharmacist in his room operates the inputting means 14 of the personal computer 3 to access to the memory means 13 through the control means 12 in the management section A for transmitting the prescription information into the memory means 15.

In the third step ST 3, the pharmacist operates the inputting means 10 to access to the memory means 15 in the editing section B for picking up information on each drug instructed in the received prescription information, which drug information can include the name, the visual image of the external appearance, the efficacy, an amount of main effective ingredient and the like of the drug. When the instructed drug is a new product and its external appearance image is not recorded yet in the memory 15, the appearance is shot by the digital camera 5 to be recorded the image into the memory 15 labeling the code number and/or name corresponding to the drug. All of these data are edited on the display 17 according to the prescription instructions into an adequate form for a patient to take the medicine. Then, in the last step ST 4, the information edited in the editing section B are transmitted to the printer C to print out in color on a sheet of paper or on a paper bag to make a document or a medicine bag including necessary information for a patient to take medicine adequately.

FIG. 4 shows an example of the medicine bag made according to the system 1. The name 22 of a patient, name 24 indicating hospital or drugstore, domicile thereof and the date of the delivery, a signature 26 of the pharmacist, and information 28 on each drug prescribed by a doctor are printed on the surface of medicine bag 20. There is given an indication of the period of time to take medicine. Item 28 is framed. A column 30 is provided indicating the name of each drug, the efficacy thereof, an amount of main effective ingredient and the like. A column 32 is provided indicating the packaged state or image 32A of the drug in full-color. Columns 34 are provided showing the time(s) to take the drug. In the columns 34, the number of drug to be taken is given which may include the instruction or notice of "before meals", "after meals" or "between meals". The directions for use of the drug may be of a concrete message of "Dose 1 tablet for 3 times in a day for every 8 hours", as given in column 36. Because the information on the drug, indication of efficacy and amount of the main effective ingredient are not always required, a special message may be given in a marginal space, when for instance, a drug contains an ingredient belonging to a separandum.

Therefore, the patient who has received the medicine bag together with the drugs accommodated therein can check the actual and prescribed drugs with an aid of the drug information printed out on the surface of bag and he can determine when any of the prescribed drugs is not accommodated in the bag or a non-prescribed drug is accommodated therein by a certain mistake. The patient can identify each of the actual drugs in the bag by checking up the same with the visual image thereof printed out on the bag prior to dosing the drug and can take the same in accordance with "Directions for use" to avoid a possible mistakes.

FIG. 5 shows a sample of another medicine bag for an external medicine. In a column of "Medicine" on this bag 40, the name of each medicine, concentration of a main effective ingredient therein, and a visual image of actual medicine are printed. For the external medicine, directions for use thereof are concretely given, for instance as "Drop lotion in your eyes 4 or 5 times in a day". An indication on efficacy and amount of the main effective ingredient are not always required for external medicines.

Instead of the medicine bag, the guiding instructions for taking the medicine may be printed out on a sheet of paper which is then attached to or inserted in a medicine bag accommodating the prescribed drugs.

Figure 6:
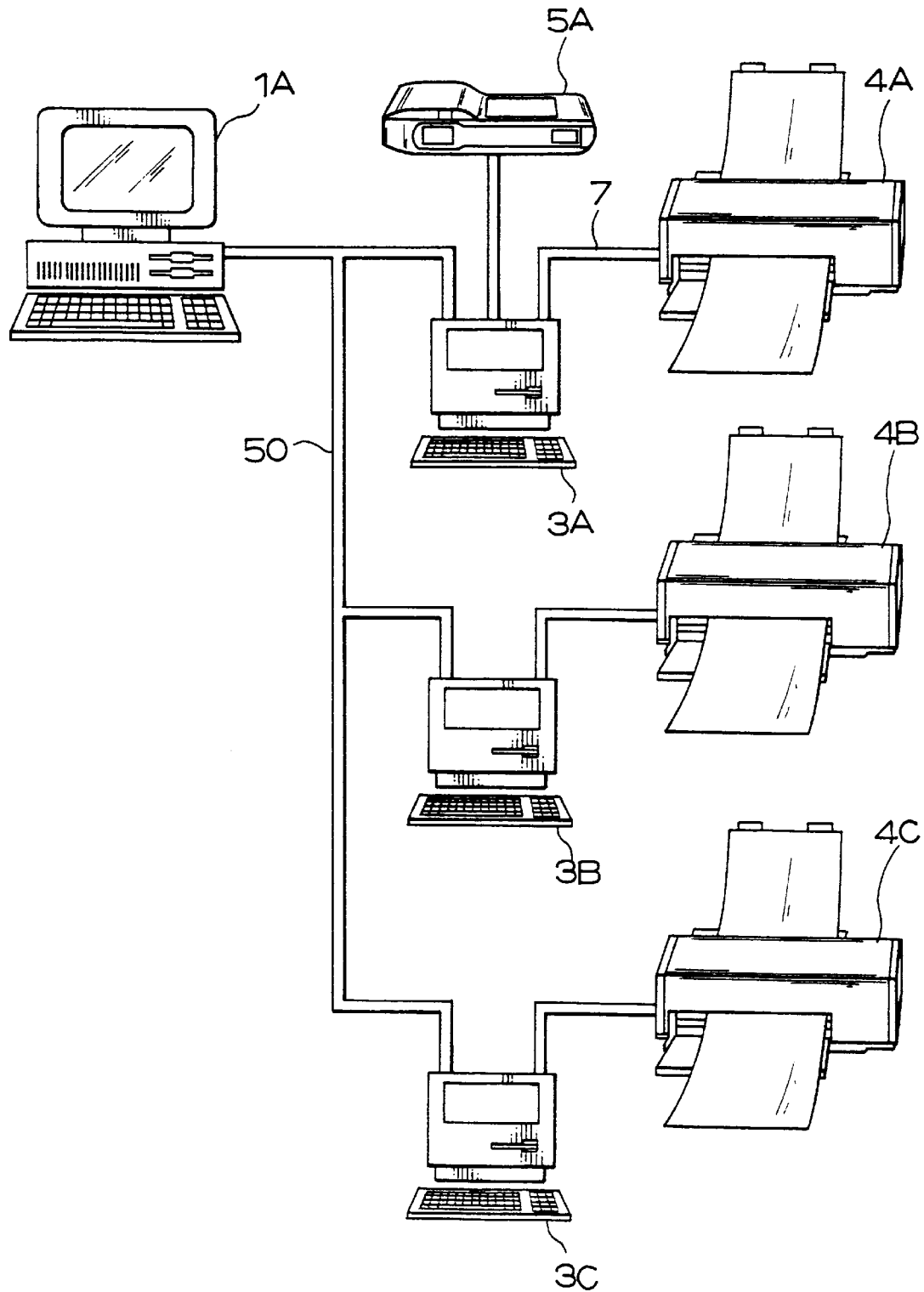
FIG. 6 is another diagrammatic illustration showing an arrangement of machines, similar to FIG. 1.

FIG. 6 shows another arrangement of machines for the invention when plural personal computers are used. In this arrangement the host computer 1A is connected with plural personal computers 3A, 3B and 3C through a LAN. The personal computers 3A, 3B and 3C have color printers 4A, 4B and 4C connected thereto respectively. A digital camera 5A is connected to only one personal computer 3A. In this case, prescription information in the host computer 1A is transmitted to each of personal computers 3A, 3B and 3C as in FIG. 1. Image data input in the computer 4A through the digital camera 5A is available to the other computer 4B and 4C through the LAN.

What is claimed is:

1. A system for dispensing and providing medicine comprising:

a computerized management section having means for a doctor to directly input information about a patient and a prescription for the patient, means for displaying the prescription information, and a main memory to store information of the prescription for each patient;

a computerized editing section connected to said management section and having memory means to store information about plural drugs inclusive of a visual image of each drug, means for accessing the main memory in the management section and the memory means storing the information about the drugs and for integrating and editing the information of the prescription of the patient and the information about the particular drugs, and means for displaying information obtained from the means for accessing, integrating and editing; and printing means connected to said editing section to print out information edited in said editing section including matters to identify each prescribed drug, dose and directions for use thereof as well as the visual image of each drug's external appearance, correlated together with patient information.

2. A system as claimed in claim 1, wherein said editing section has means for inputting a visual image of drug, which is selected from the group consisting of a digital camera, a video camera, a CCD video camera and an image scanner.

3. A system as claimed in claim 1, wherein the visual image of the drug is that of a packaged state thereof.

4. A system as claimed in claim 1, wherein the information about the drug includes the efficacy of a main effective ingredient contained therein.

5. A system as claimed in claim 1, wherein said printing means print out the information edited in said editing section on a paper bag.

* * * * *